United States Patent [19]

Bay

[11] Patent Number: 4,754,072
[45] Date of Patent: Jun. 28, 1988

[54] PREPARATION OF THIOPHENOLS FROM PHENOLS

[75] Inventor: Elliott Bay, Ridgefield, Conn.

[73] Assignee: Stauffer Chemical Company, Westport, Conn.

[21] Appl. No.: 23,182

[22] Filed: Mar. 9, 1987

[51] Int. Cl.$^4$ .................. C07C 148/00; C07C 149/28
[52] U.S. Cl. ........................................ 568/67; 568/68; 558/257
[58] Field of Search ..................... 558/257; 568/67, 68

[56] References Cited

PUBLICATIONS

Kazimi et al, "J. Amer. Chem. Soc.", vol. 77, pp. 2479–2482 (1955).

Newman, "J. Chem. Soc.", vol. 31, pp. 3980–3984 (1966).

Rod's Chemistry of Carbon Compounds", supplement to 2nd ed, Supplement to vol. 111, pp. 247–249 (1983).

*Primary Examiner*—Werren B. Lone
*Attorney, Agent, or Firm*—Joel G. Ackerman; Richard P. Fennelly

[57] ABSTRACT

Thiophenols are formed from phenols by first reacting a phenol with thiophosgene to form an aryl chlorothionoformate which is subjected to a halogen exchange reaction using an alkali metal fluoride to yield the corresponding fluorothionoformate. This fluorothionoformate is then rearranged to the corresponding fluorothiolformate by heating and the resulting fluorothiolformate is then hydrolyzed to yield the desired thiophenol.

8 Claims, No Drawings

PREPARATION OF THIOPHENOLS FROM PHENOLS

BACKGROUND OF THE PRESENT INVENTION

1. Field of the Present Invention

The present invention relates to a synthetic method for making thiophenols from phenols.

2. Description of the Prior Art

It has been reported that the rearrangement of diaryl thionocarbonates to diaryl thiolcarbonates via the Schonberg rearrangement offered a way of converting phenols to thiophenols (J. of the Amer. Chem. Soc., Vol. 77, pp. 2479-2482 (1955)). This reported procedure involved the preparation of symmetrical thionocarbonates by the action of thiophosgene on the phenols in two stages or, more conveniently, by treatment of a benzene solution of two moles of the phenol and one mole of thiophosgene with dry pyridine. This type of procedure was noted by M. S. Newman et al. in J. of the Amer. Chem. Soc., Vol. 31, pp. 3980-3984 (1966), but was indicated as being limited to a maximum yield possible of 50% with respect to conversion of a phenol to the corresponding thiophenol. Newman et al. instead proposed conversion of the phenol to the O-aryl dialkylthiocarbamate with its conversion to the S-aryl dialkylthiocarbamate and thence to the thiophenol.

More recently, various preparative methods for preparing thiophenols from phenols was described in Rodd's Chemistry of Carbon Compounds, Supplements to the 2nd Edition, Supplement to Vol. III, pp. 247-249 (1983). Among the routes that were mentioned was the transformation of the thionocarbonates to the thiolcarbonate using the Schonberg rearrangement, as well as a variation developed by Y. Araki et al. wherein the phenol is reacted with the compound of the formula ClC(S)R.

SUMMARY OF THE PRESENT INVENTION

The present invention is a novel method for forming thiophenols from phenols which comprises the first step of reacting a phenol with thiophosgene to form an aryl chlorothionoformate. This aryl chlorothionoformate is then subjected to a halogen exchange reaction using an alkali metal fluoride to yield the corresponding fluorothionoformate. The fluorothionoformate is then heated to rearrange it to the corresponding fluorothiolformate which is then hydrolyzed to yield the desired thiophenol.

In addition to the foregoing, it is believed that the heating of the fluorothionoformate to rearrange it to the corresponding fluorothiolformate is novel. Similarly, the halogen exchange reaction, rearrangement of the fluorothiolformate and subsequent hydrolysis step are deemed to be novel. Finally, the combination of the above-described rearrangement and subsequent hydrolysis steps is deemed to be novel as well.

DETAILED DESCRIPTION OF THE PRESENT INVENTION

The first step in the process of the claimed invention is the reaction of a phenol with thiophosgene to form an aryl chlorothionoformate. The phenol has the general formula ArOH with the aryl moiety being either unsubstituted or substituted with non-interfering substituents such as halogen, alkoxy, alkyl and the like. Bulky groups, such as t-butyl, particularly if in a sterically crowding position around the —OH moiety (e.g., as in 2,6-di-t-butyl phenol) should not be employed. The reaction is preferably between substantially equimolar amounts of the phenol and with thiophosgene in an aqueous/solventsystem under temperatures that are effective to cause the reaction to proceed (from about 0° C. to about 10° C.). The phenol is dissolved in an aqueous hydroxide solution and reacted with thiophosgene in a water immiscible solvent. The salt of the phenol migrates to the water layer leaving the solvent layer with the desired product. This layer can be washed with acid and water and dried. The resulting aryl chlorothionoformate has the generalized formula ArOC(S)Cl where Ar represents a phenyl ring which may be substituted as mentioned above.

The second step of the present reaction involves taking the chlorothionoformate formed in the preceding step and subjecting it to a halogen exchange reaction using an alkali metal fluoride such as sodium fluoride. This exchange reaction is preferably conducted in a suitable solvent such as acetonitrile or dimethylformamide at temperatures ranging from about 20° C. to about 200° C. in order to form the corresponding fluorothionoformate. The sodium fluoride is soluble whereas sodium chloride by-product is not. The sodium chloride therefore precipitates out of the solvent to aid in driving the reaction to completion. The process step is preferably conducted under refluxing solvent conditions. The fluorothionoformate has the formula ArOC(S)F.

In the next step of the procedure, the fluorothionoformate from the halogen exchange reaction is rearranged to the corresponding fluorothiolformate by heating, e.g., at temperatures of from about 200° C. to about 500° C. This step is a very hot, very fast vapor phase reaction, preferably in an inert atmosphere in a tube reactor. The resulting fluorothiolformate has the generalized formula ArSC(O)F.

The last step of the present process involves the hydrolysis of the thiolformate resulting from the preceding step to give the desired thiolphenol (or aryl mercaptan) of the formula ArSH.

The foregoing process is further illustrated by the Examples which follow.

EXAMPLE 1

This describes the reaction of thiophosgene and phenol to form an aryl chlorothionoformate. Thiophosgene (77 gm, 0.67 mole) and chloroform (400 ml) were placed in a two liter four neck, round bottom flask fitted with a thermometer, calcium chloride drying tube, addition funnel, and mechanical stirrer. This solution was cooled to 0° C.–5° C. by placing the flask in an ice bath.

Phenol (63 gm, 0.7 mole) was dissolved in 5% aqueous sodium hydroxide (600 ml) in a separate flask and was cooled to 0° C.–5° C. This phenol solution was added portionwise to the addition funnel (while the remainder of the phenol solution was kept in an ice cooled flask) and was added dropwise to the stirred thiophosgene solution. The addition rate was adjusted so that the reaction temperature remained below 10° C. The reaction was stirred for one hour after addition was complete at 0° C.–5° C. The reaction mixture was placed in a separatory funnel, and the chloroform layer was removed.

The chloroform layer which had been removed was washed with 5% hydrochloric acid (250 ml) and water (250 ml). The extract was dried with magnesium sulfate and concentrated. Vacuum distillation gave 94 gm of phenyl chlorothionoformate (bp: 51° C.–58° C./8 mm Hg). The yield was 81%.

EXAMPLE 2

This illustrates the halogen exchange reaction of the product of Example 1 using sodium fluoride.

Phenyl chlorothionoformate (20 gm, 0.116) was added in one portion to a stirred slurry of sodium fluoride (10 gm, 0.238 mole) and acetonitrile. This reaction mixture was refluxed under a nitrogen atmosphere for seven hours. The reaction mixture was then cooled to room temperature, filtered, and the solvent distilled off at atmospheric pressure. Vacuum distillation gave 12.5 gm of phenyl fluorothionoformate (bp: 60° C./7 mm Hg). The yield was 69%.

EXAMPLE 3

This Example shows rearrangement of the fluorothionoformate of Example 2 to yield the corresponding fluorothiolformate. Phenyl fluorothionoformate (5 gm, 0.032 mole) was pumped with a syringe pump at a rate of 1 ml/hr into a 2 foot by 0.25 inch outer diameter 316 stainless steel tube reactor. The reactor tube was at 400° C. Nitrogen was flushed through the reactor tube at 6 ml/hr. The reaction product was collected in a dry ice cooled trap attached to the exit of the reactor tube. Vapor phase chromatography (VPC) analysis of the product showed only phenyl fluorothiolformate with no unrearrangement starting material present. The amount of product collected was 1.2 gm for a yield of 24%.

EXAMPLE 4

This shows hydrolysis of the fluorothiolformate of Example 3 to thiophenol. Phenyl fluorothiolformate (1 gm), 10% aqueous sodium hydroxide (10 ml), and ethanol (10 ml) were mixed and stirred at room temperature for four hours. The reaction mixture was made acidic with concentrated hydrochloric acid. The only organic reaction product present by VPC analysis was thiophenol.

The foregoing Examples should not be construed in a limiting sense, since they are merely set forth to illustrate certain specific embodiments of the present invention. The scope of protection that is sought is set forth in the claims which follow.

I claim:

1. A method for forming thiophenols from phenols which comprises:
   (a) reacting a phenol with thiophosgene to form an aryl chlorothionoformate;
   (b) conducting a halogen exchange reaction between the chlorothionoformate and an alkali metal fluoride to yield the corresponding fluorothiono formate;
   (c) heating the fluorothionoformate to a temperature of from about 200° C. to about 500° C. to rearrange it to the corresponding fluorothiolformate; and
   (d) hydrolyzing the fluorothiolformate to yield the thiophenol.

2. A method which comprises heating a fluorothionoformate to a temperature of from about 200° C. to about 500° C. to rearrange it to the corresponding fluorothiolformate.

3. A method for forming fluorothiolformates from phenols which comprises:
   (a) reacting a phenol with thiophosgene to form an aryl chlorothionoformate;
   (b) conducting a halogen exchange reaction between the chlorothionoformate and an alkali metal fluoride to yield the corresponding fluorothionoformate; and
   (c) heating the fluorothionoformate to a temperature of from about 200° C. to about 500° C. to rearrange it to the corresponding fluorothiolformate.

4. A method for forming thiophenols from chlorothionoformates which comprises:
   (a) conducting a halogen exchange reaction between a chlorothionoformate and an alkali metal fluoride to yield the corresponding fluorothionoformate;
   (b) heating the fluorothionoformate to a temperature of from about 200° C. to about 500° C. to rearrange it to the corresponding fluorothiolformate; and
   (c) hydrolyzing the fluorothiolformate to yield the thiophenol.

5. A method as claimed in either claim 1 or 3 wherein the phenol is non-substituted.

6. A method as claimed in either claim 1 or 3 wherein the reaction of the phenol and thiophosgene is conducted in an aqueous/solvent system.

7. A method as claimed in either claim 1, 3 or 4 wherein the alkali metal fluoride is sodium fluoride.

8. A method as claimed in either claim 1 or 4 wherein the thiophenol is an unsubstituted thiophenol.

* * * * *